United States Patent [19]

Rullier et al.

[11] Patent Number: 4,863,186

[45] Date of Patent: Sep. 5, 1989

[54] SAFETY BINDING

[75] Inventors: Pierre Rullier; Bertrand Besnier, both of Annecy, France

[73] Assignee: Salomon S.A., Annecy, France

[21] Appl. No.: 52,415

[22] Filed: May 21, 1987

[30] Foreign Application Priority Data

May 22, 1986 [FR] France ............................... 86 07839

[51] Int. Cl.⁴ ............................................... A63C 9/08
[52] U.S. Cl. ..................... 280/626; 280/618; 280/620; 280/628; 280/636
[58] Field of Search ............... 280/626, 628, 618, 620, 280/634, 615, 614

[56] References Cited

U.S. PATENT DOCUMENTS

| 2,686,059 | 8/1954 | Whitaker | 280/614 |
| 3,797,843 | 3/1974 | Salomon | 280/618 |
| 4,008,907 | 2/1977 | Murata | 280/620 |
| 4,027,896 | 6/1977 | Frechin | 280/618 |
| 4,035,001 | 7/1977 | Jungkind et al. | 280/618 |
| 4,140,332 | 2/1979 | Beyl | 280/620 |
| 4,165,889 | 8/1979 | Weinstein et al. | 280/626 |
| 4,188,045 | 2/1980 | Marker | 280/618 |

FOREIGN PATENT DOCUMENTS

| 1926108 | 11/1970 | Fed. Rep. of Germany | 280/614 |
| 3441663 | 7/1985 | Fed. Rep. of Germany | 280/618 |
| 2157686 | 6/1973 | France . | |
| 2248680 | 5/1975 | France . | |
| 2269982 | 12/1975 | France . | |
| 2368973 | 5/1978 | France . | |
| 2397851 | 2/1979 | France . | |
| 2502019 | 9/1982 | France . | |
| 2527464 | 12/1983 | France . | |

Primary Examiner—David M. Mitchell
Attorney, Agent, or Firm—Sandler & Greenblum

[57] ABSTRACT

A binding for retaining a boot on a ski. The binding is provided with a jaw for retaining one end of a boot against the ski, and a support on which the jaw is mounted. The support itself is connected to two arms mounted on the ski. These two arms are separated by a distance less than the width of a sole of the boot which the binding retains on the ski.

64 Claims, 12 Drawing Sheets

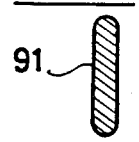
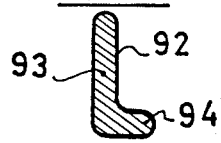
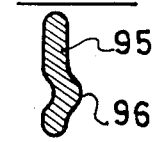
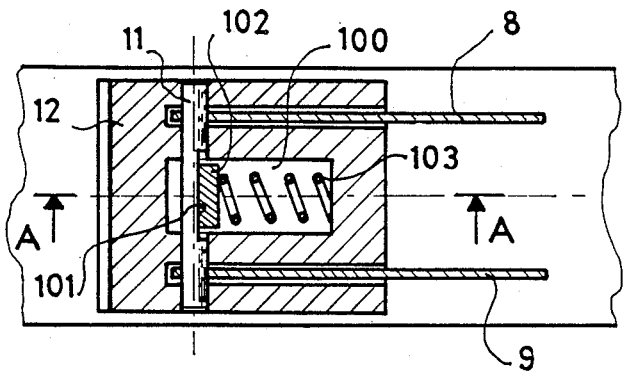
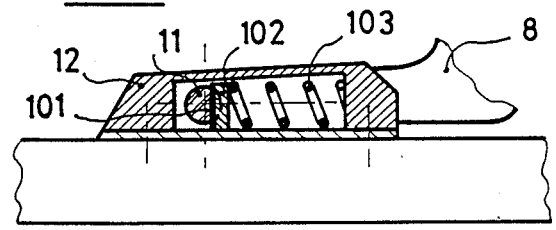
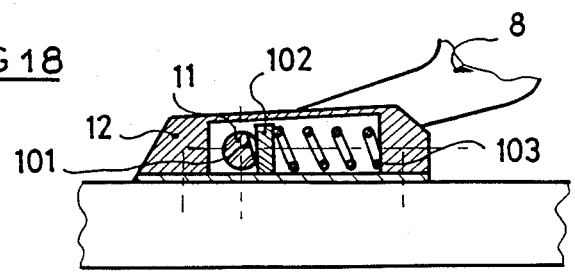
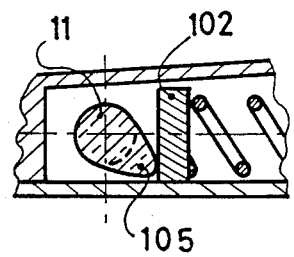

SAFETY BINDING

BACKGROUND OF THE INVENTION

1. Field of the Invention

The invention relates to a safety binding for securing a ski boot onto a ski. More specifically, the invention relates to a binding adapted to retain one end of the boot in contact with the upper surface of the ski.

2. Description of Background and Relevant Information

Bindings for retaining a portion of the boot against the upper surface of the ski, particularly of the rear binding type, are known in the art. Such bindings generally have a jaw adapted to retain one end of the boot, particularly the rear end.

The jaw is adapted for movement in a vertical plane defined by the length of the ski, and, conventionally, is itself journalled around a horizontal axis transverse to the length of the ski.

The jaw is carried by support means connected to the ski; elastic energization means elastically bias the jaw toward the upper surface of the ski.

Amongst safety bindings of this type, the invention relates more particularly to bindings connected to the ski by two lateral arms. These arms are journalled on a transverse axis mounted on the ski adjacent to the end of the boot adapted to be retained on the ski.

Known bindings of this type are disclosed in French Pat. No. 2,368,973, which is the equivalent of U.S. Pat. No. 4,140,332, French Pat. No. 2,299,883, which is the equivalent of U.S. Pat. No. 4,035,001, and French Pat. No. 2,502,019, which is the equivalent of West German Pat. No. 3,210,477, the disclosure of all of which are hereby incorporated by reference thereto.

Generally for such bindings, the lateral arms which connect the body to the ski are disposed around the exterior of the the boot sole; each arm is linked to the ski outside the sole's contour, at the level of the ear of a base plate; most often, the linkage is situated above the lower surface of the sole. Because they are situated on each side of the sole, the ears likewise allow the sole of the boot to be laterally wedged in place.

The principal disadvantage of such bindings is that the lateral arms, as well as the ears which bind these arms to the ski, laterally border both the contour of the sole, and the lateral edges of the ski. This consequence occurs because these bindings, in effect, are wider than the width of the ski, and wider than the width of the boot at the level of the sole. As a result, the projecting portions of these bindings can get caught on the snow and interfere with the movement of the ski in unexpected and undesireable ways.

Preferably, the lateral arms are elastically biased towards the ski to facilitate the insertion of the boot in the binding. Another disadvantage of bindings of this type presently known in the art is that they require auxiliary springs to perform this function. Such springs thus complicate the assembly of the binding, and likewise increase its cost.

One of the purposes of the invention is to overcome these disadvantages, and provide a binding, of the above-indicated type, wherein each element does not extend laterally beyond the exterior contour of the sole of the boot.

Another purpose of the invention is to provide a binding wherein elastic biasing of the arms towards the ski is accomplished in a simple fashion, without requiring auxiliary springs.

The safety binding according to the invention comprises: a jaw which is adapted to retain one end of the boot, and is adapted to move in at least one direction along a vertical plane; a support for the jaw; two lateral arms connecting the jaw to the ski; an axis, on which the lateral arms are journalled, mounted perpendicular to the length of the ski, and situated adjacent to the boot end, under the sole; and elastic energization means for elastically biasing the jaw toward the ski.

The two lateral arms of the binding are transversely spaced by a distance which is less than the width of the sole at the boot end retained by the binding. Each arm is bent, and is provided with first and second segments. Each first segment is connected at one end to the journal axis. When the binding is disposed in the rest position, the first segment of each arm extends substantially parallel to the length of the ski under the level of the boot sole; the second segment is bent upwardly and oriented toward the jaw support.

The elastic energization means, preferably in the form of a spring, bias the binding, and, in particular, the lateral arms of the binding, towards the ski.

The binding illustrated in the various FIGS. is of the heel type, i.e., is adapted to retain the rear end, particularly the heel, of a boot. However, the invention is equally applicable to a binding adapted to retain the front end, particularly the toe, of a boot.

The invention is described with reference to the following drawings, which are provided by way of example, not limitation.

SUMMARY OF THE INVENTION

The invention pertains to a binding for retaining a boot on a ski. The binding comprises means for pressing one end of said boot against said ski, means for supporting said pressing means, and at least two connecting members comprising means for connecting said supporting means to said ski; said at least two connecting members are spaced apart by a distance less than the width of a sole of the boot end which is adapted to be retained by the binding. The binding of the invention is equally suitable for retaining the front end, or, more specifically, the toe, of the boot, as well as the rear end, or, more specifically, the heel, of the boot.

Preferably, the at least two connecting members are separated by a distance less than the width of the ski. Most preferably, the at least two connecting members comprise two arms mounted on the ski to pivot into and out of a retracted position; in the retracted position, at least a portion of each arm is positioned under a surface for supporting the boot end retained.

The two arms may be journalled about an axis perpendicular to the length of the ski. In a preferred embodiment, each of the two arms so journalled comprises a first arm segment mounted on the axis for pivoting, and a second arm segment connected to the supporting means; in the indicated retracted position, at least a portion of the first arm segments along their lengths are positioned under the surface for supporting the boot end, and the second arm segments are angled upwardly towards the means for supporting pressing means.

In one embodiment of the binding of the invention, the pressing means is affixed to the supporting means, and the supporting means and the second arm segments are pivotably mounted with respect to one another. In another embodiment, the supporting means is affixed to the second arm segments, and the pressing means and supporting means are pivotably mounted with respect to one another.

The indicated axis may be mounted on the ski. Where the axis is mounted on the ski, the ski defines recessed areas; at least a portion of the first arm segments, along their length, are positioned in these recessed areas when the arms are positioned in the indicated retracted position.

In another embodiment, the axis may be mounted on a platform, or housing, itself adapted to be mounted on the ski. This housing comprises at least one surface to which each of the first arm segments is attached; the surface for supporting the boot end includes the upper surface of this housing. Preferably, the housing is attached to the upper surface of a ski.

The housing may comprise recessed areas; in such instance, at least a portion of the first arm segments, along their length, are positioned in these recessed areas when the arms are positioned in the retracted position. In a preferred embodiment, the recesses are spaced inwardly from opposed exterior sides of the housing.

The first segment of each arm may be connected to its second segment. The two arms may themselves be connected by a cross-member affixed to each of the arms at the point of connection between the first and second arm segments.

The at least one surface to which each of the first arm segments is attached may comprise two exterior sides of the housing. In this instance, preferably, the first arm segments are parallel to one another and the second arm segments are also parallel to one another; further, the first arm segments are spaced apart by a distance greater than the distance spacing the second arm segments apart, and the first and second arm segments are connected by angled intermediate arm segments.

Alternatively, the indicated two exterior sides of the housing may be oppositely angled, with at least a portion of said first arm segments likewise being oppositely angled.

In a preferred embodiment, the binding of the invention further comprises means for biasing the arms toward the ski. The binding may have a pivotable axis, with the first arm segments being journalled on the axis; the biasing means preferably comprises elastic energization means associated with this axis. The elastic energization means preferably comprises a compression spring aligned substantially perpendicular to the axis, both biasing the axis and being compressed by the pivoting of the axis.

In a preferred embodiment, the axis comprises a substantially cylindrical member having a planar surface located between its two ends. The compression spring abuts this planar surface.

In another preferred embodiment, the axis comprises an eccentric member which abuts the compression spring.

The binding may be mounted on a housing which is itself adapted to be mounted on the ski. The housing may be mounted to slide along the length of the ski, with the compression spring comprising means for biasing the housing along the length of the ski towards the boot end retained by the binding; in this embodiment, the axis, mounted on the housing, compresses the spring against abutment means mounted on the ski.

The indicated abutment means may be affixed to the ski, or, alternatively, may be mounted on means for adjusting the position of the abutment means along the length of the ski.

In the embodiment of the invention incorporating a housing mounted on the ski, the axis may be mounted for sliding movement in this housing, in a slot extending in a direction substantially parallel to the length of the ski; in this embodiment, the compression spring biases the axis along the length of the ski toward the boot end retained by the binding, and the axis compresses the spring against abutment means mounted on the housing.

In conjunction, as described above, with the mounting of the axis in a slot for sliding movement, the housing may also be mounted in a stationary position with respect to the ski.

The abutment means mounted on the housing may be affixed to the housing, or, alternatively, may be mounted on means for adjusting its position within the housing. The position adjusting means for this abutment may comprise a screw mounted in the housing. In yet another alternative, this abutment means may be an interior surface of the housing.

The housing mounted on the ski may include an inclined ramp; in this embodiment of the binding of the invention, the two arms are connected by a cross-member which is adapted to slidably abut this ramp when the compression spring is not compressed. The pivoting of the arms raises the cross-member along the ramp; retaining a boot end on the ski spaces the cross member from the ramp. In a preferred embodiment, the ramp is provided with a lip to limit the rise of the cross-member during the pivoting of the arms.

Where the binding of the invention incorporates a housing, the housing may be mounted to pivot on the ski. Preferably, the indicated pivotable housing comprises at least one surface to which each of the first arm segments is attached; the surface for supporting the boot end includes the upper surface of the housing.

The invention further pertains to a binding for retaining a ski boot on a ski. The binding is provided with a jaw, adapted to move in at least one direction along a vertical plane, for retaining one end of the boot. Elastic energization means are provided for biasing the jaw towards the ski. The binding is further provided with means for supporting the jaw, and at least two arms aligned along the length of the ski connecting the jaw-supporting means to the ski. The two arms are aligned along the length of the ski, and spaced apart by a distance less than the width of the sole of the boot end adapted to be retained; further, the two arms are journalled about an axis perpendicular to the length of the ski in order to pivot into and out of a retracted position.

In the retracted position, each arm comprises a first segment positioned under a surface for supporting the boot end, and aligned substantially parallel to the length of the ski, and a second arm segment angled upwardly towards the jaw-supporting means.

The jaw may be affixed to the jaw-supporting means, with the jaw-supporting means being journalled on the arm. Alternatively, the jaw may be journalled on the jaw-supporting means, with the jaw-supporting means affixed to the arms.

The axis may be mounted on a housing which is itself adapted to be mounted on the ski. This housing comprises at least one surface to which each of the first arm segments is attached. The surface for supporting the boot end includes the upper surface of this housing.

The housing may further comprise recessed areas extending along at least a portion of the housing, wherein a portion of each of the first arm segments, when in its retracted position, is positioned in one of these recessed areas.

Preferably, the arms connecting the jaw-supporting means to the ski are vertically pivotable.

In a preferred embodiment of the invention, the first arm segments are substantially parallel to one another, and the second arm segments are also substantially parallel to one another. The first arm segments are spaced apart by a distance greater than the distance spacing apart the second arm segments, and the first and second arm segments are connected by angled intermediate arm segments.

In the embodiment of the invention incorporating a housing adapted to be mounted on the ski, the housing may include two oppositely angled exterior side surfaces, with at least a portion of the first arm segments likewise oppositely angled.

The arms connecting the jaw-supporting means to the ski in the binding of the invention may be connected by a cross-member.

Regarding the axis on which the arms are journalled, specifically, the axis may be attached to free ends of the first arm segments and pivotably mounted on the housing; in this embodiment, the elastic energizing means comprise means for biasing the axis. The axis may comprise a substantially cylindrical member having a planar surface between two ends of the axis, with the elastic energizing means comprising a compression spring which abuts this planar surface. Alternatively, the axis may comprise an eccentric member which abuts a compression spring.

The elastic energizing means may comprise means for biasing the binding towards the boot end adapted to be retained by the binding.

The housing adapted to be mounted on the ski may include an inclined ramp, with the axis being slidably mounted in a slot in the housing; this slot extends in a direction substantially parallel to the length of the ski. In this embodiment, the biasing means further comprises means for biasing the housing along the legth of the ski towards the support surface; the two arms are connected by a cross-member which is adapted to slidably abut the ramp. The cross-member abuts the ramp when no boot is positioned on the surface, and comprises means for compressing the elastic energization means when the cross-member rises up the ramp.

The inclined ramp and the housing may comprise a single member. Alternatively, the inclined ramp and the housing may comprise two members attached to each other.

The housing may be mounted to pivot on an axis perpendicular to the length of the ski.

In the binding of the invention, the axis may be mounted on the ski. In this embodiment of the invention, the upper surface of the ski is provided with recessed areas extending along at least a portion of the length of the ski. The first arm segments are positioned in these recessed areas when in their retracted position.

BRIEF DESCRIPTION OF THE DRAWINGS

FIGS. 13-15 show different transverse sections of different embodiments of the lateral arms;

FIG. 16 is a top cutaway view of the housing of the binding of FIG. 1, exposing the means for biasing the arms toward the skis, and illustrating the elastic return of the arms in the direction of the ski;

FIG. 17 is a side cutaway view taken along line AA of the binding of FIG. 16, also exposing the biasing means, and showing the arms in lower position;

FIG. 18 is another side cutaway view as in FIG. 17, showing the arms in lifted positions;

FIG. 19 shows an alternative embodiment of the biasing means of the binding of FIG. 17;

DESCRIPTION OF PREFERRED EMBODIMENTS

Figure 1:
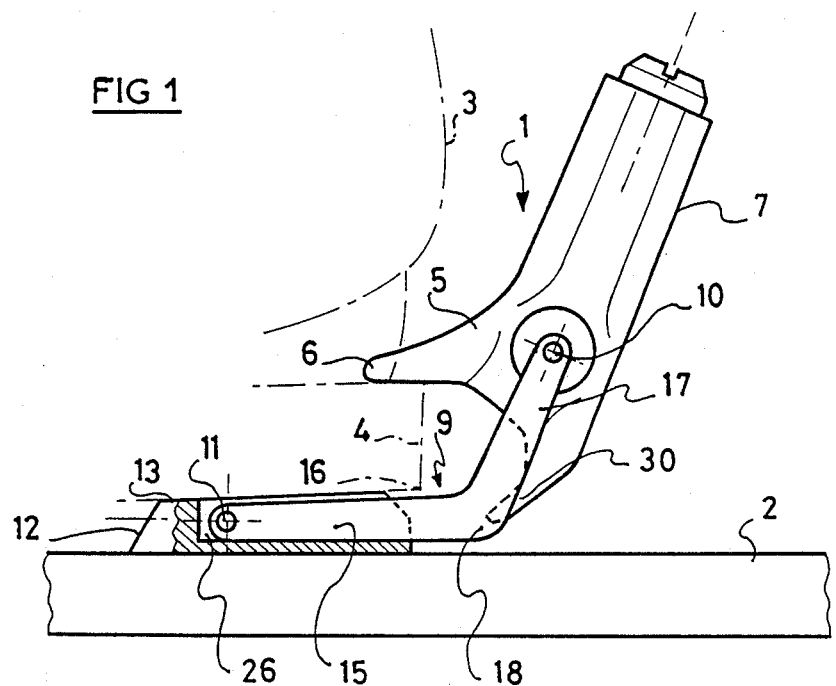
FIG. 1 is a side view of a general embodiment of the binding according to the invention, mounted on a ski.

FIG. 1 shows a general embodiment of the binding of the invention, binding 1, mounted on the upper surface of the ski 2.

Binding 1 is adapted to retain the rear end of the boot in contact with the ski, and to release the boot end when it exerts, against the binding, a pressure which exceeds a predetermined threshold.

FIG. 1 further outlines, in dashed lines, the area occupied by rear portion 3 of a boot kept in contact with a ski by binding 1, particularly at the heel of sole 4.

Binding 1 of FIG. 1 comprises jaw 5, which is adapted to retain the rear end of the boot, particularly by means of sole grip 6, which grips the upper edge of sole 4.

Jaw 5 extends from sole grip 6 in the form of body 7, thereby forming, with body 7, a single piece assembly. Body 7 is itself connected to the ski by two lateral arms 8 and 9; specifically, on the upper end of the arms, body 7 is journalled around transverse axis 10.

Jaw 5 and body 7 are thus mounted for rotation around axis 10, in the vertical plane defined by the length of the ski.

Binding 1 further comprises elastic energization means which bias jaw 5 toward the ski. When the force exerted by the boot on the binding exceeds a predetermined threshold, these elastic energization means allow jaw 5 and body 7 to pivot, thereby freeing sole 4 from the boot.

These elastic energization means are positioned within body 7, and are of a type known in the art. For example, they can be the same type as those described in the French and U.S. materials previously described, and incorporated herein by reference. Accordingly, they are not described herein in further detail.

Lateral arms 8 and 9, having body 7 journalled on their upper ends, are themselves journalled on their lower ends on transverse axis 11. In the embodiment shown in FIG. 1, transverse axis 11 is mounted on housing 12.

Housing 12 is itself mounted on the upper surface of ski 2 by any suitable means. The housing may be directly mounted on the upper surface of the ski; further, it may be mounted on length adjustment apparatus of a type known in the art, on which it is slidably mounted and blocked. Housing 12 is provided with upper surface 13, on which the boot rests, in the normal skiing position. Accordingly, transverse axis 11 is situated under the heel of the boot.

In the binding of the invention, arms 8 and 9 are transversely spaced by a distance less than the width of boot sole 4 at the heel.

It is known in the art that the shape of ski boot soles is generally standardized, particularly as to width and radius curvature of the sole at its heel. For example, according to DIN 7880 standard, the width of the boot at the heel is 69 mm. for an adult boot, and 62 mm. for a junior boot.

In a preferred embodiment of the binding of the invention, the distance between the two lateral arms 8 and 9 is less than the appropriate standardized width.

Furthermore, each arm 8 and 9 is angled, and provided with first and second arm segments. When the arm is retracted, first arm segment 15 lies substantially parallel to ski 2, under the sole of the boot. In this position, first arm segment 15 extends from journal axis 11 towards the position occupied by lower end edge 16 of boot 4.

Connected to first arm segment 15 is second arm segment 17. Second arm element 17 is angled upwardly toward body 7, and is mounted at its end on journal axis 10.

As shown in FIG. 1, angle 18 of each of arms 8 and 9, situated between respective first arm segment 15 and second arm segment 17, is also situated adjacent lower end edge 16 of sole 4; between them, the two arm segments 15 and 17 intersect to form an angle of approximately 90°. This angle can also be less than, or more than, 90°, without departing from the scope of the invention.

Figure 2:
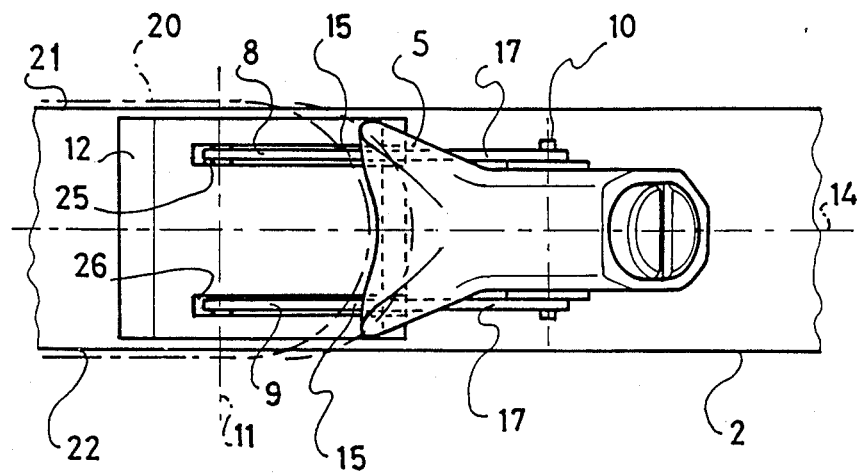
FIG. 2 is a top view of the binding of FIG. 1.

As shown in FIG. 2, no portion of the binding of the invention extends laterally beyond the exterior contour of the sole of a boot, schematically shown by dashed lines 20. Further, no portion of the binding extends laterally beyond lateral sides 21 and 22 of ski 2.

FIG. 2 furthermore illustrates, for a general embodiment of the invention, the relative arrangement of housing 12 and of lateral arms 8 and 9, or, more particularly, their first arm segments 15. According to this embodiment, housing 12 is rectangular, and has a width less than that of the ski. Two recessed areas 25 and 26 are situated in the central portion of housing 12. These grooves are parallel, or substantially parallel, to the length of the ski; they extend from journal axis 11 of arms 8 and 9 towards the rear of the housing, onto which they open.

The width of each of recessed areas 25 and 26 is slightly greater than that of a transverse section of its corresponding first arm segment 15; the height of each recessed area is also equal to or greater than the length of a transverse section of its corresponding first arm segment 15. Accordingly, when the binding is in the rest position, first arm segments 15 of arms 8 and 9 retract, at least over a portion of their length, into recessed areas 25 and 26.

Journal axis 11 is mounted on housing 12 to allow for this retraction; preferably, it is mounted at least substantially within housing 12. Most preferably, journal axis 11 is disposed entirely within housing 12 so as, from a side view, not to protrude above housing 12.

In this fashion, each of recessed areas 25 and 26 provides segment 15 of its respective arm 8 or 9 with two transverse guidance surfaces, which laterally define the grooves.

Figure 3:
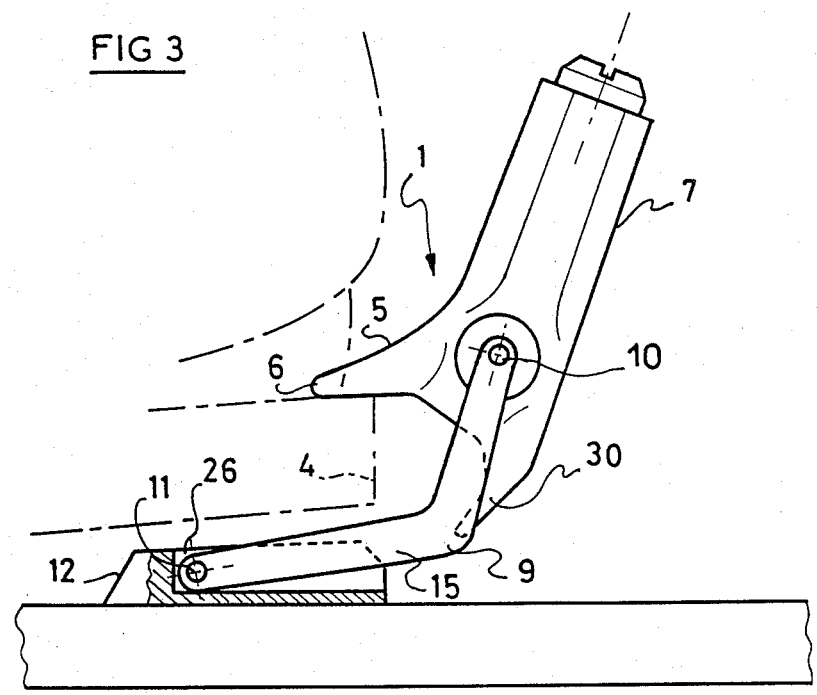
FIG. 3 demonstrates the rotation of the arms of FIG. 1 with respect to the ski.

FIG. 3 shows the binding of FIGS. 1 and 2 subjected to an upward pressure by sole 4.

Under the effect of this pressure, arms 8 and 9 pivot around journal axis 11. In the course of this movement, first arm segments 15 of arms 8 and 9 are lifted from their seat, provided by recessed areas 25 and 26. Further, body 7 and jaw 5 can be disposed to pivot around axis 10 in conjunction with the movement of arms 8 and 9.

As shown in FIG. 3, binding 1 is configured so that exerting sufficient upward pressure on the binding will cause it to release, thereby freeing the boot. If the pressure exerted is less than sufficient, cessation of this pressure will cause the boot to return to the normal skiing position, resting on housing 12.

Figure 4:
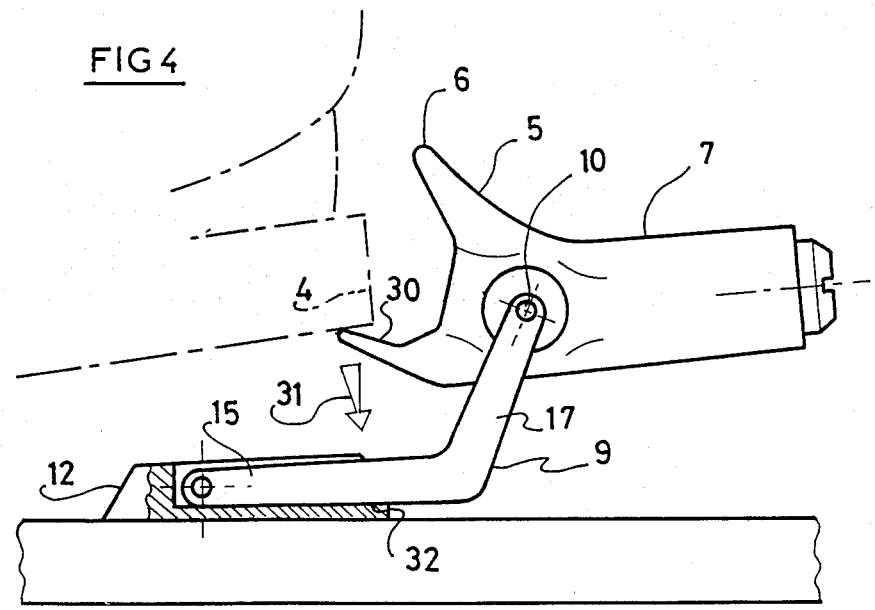
FIG. 4 shows the binding of FIG. 1 positioned for insertion of the boot.

The action of the binding during the process of inserting a boot is shown in FIG. 4. In a conventional manner, body 7 is first pivoted rearwardly; on the other side of axis 10, tongue 30 thereby assumes an approximately horizontal position. To insert the boot, the user places the rear end of the sole 4 on tongue 30 and exerts a downward pressure, schematically shown by arrow 31.

This downward pressure is transmitted to angled arms 8 and 9. Under the effect of this pressure, first segments 15 of arms 8 and 9 come to abut a lower surface. This lower surface can be lower surface 32 of recessed areas 25 and 26.

Journal axis 10 of body 7 is thereby stabilized during exertion of pressure by the boot along the entire length of tongue 30. The stabilization of journal axis 10 allows for the pivoting of body 7, and the positioning of sole grip 6 on the rear end of sole 4. The conventional means known in the prior art for providing this stabilizing function are here absent, the stabilizing function being performed by arms 8 and 9 themselves.

Figure 5:
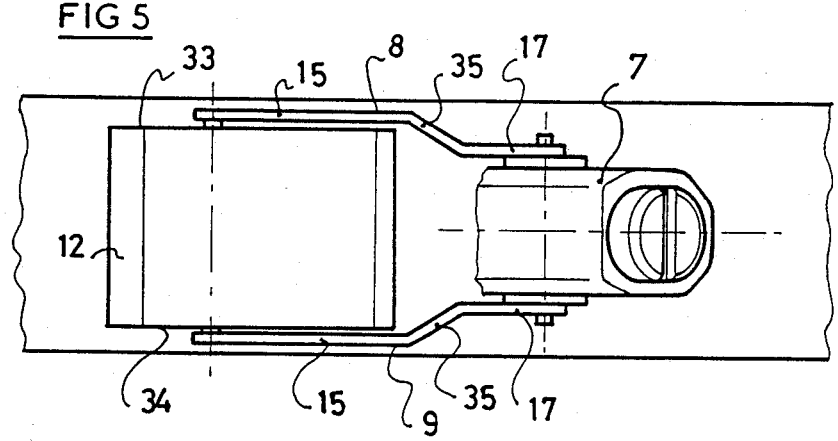
FIGS. 5-7 are top views of specific alternative embodiments of the binding of the invention, varying with respect to the relative position of the arms and of the housing.

According to the embodiment shown in FIG. 5, first arm segments 15 or arms 8 and 9 are parallel to one another, and extend respectively on either side of housing 12. Accordingly, lateral exterior surfaces 33 and 34 of housing 12 are parallel to one another, and the spacing of first arm segments 15 of arms 8 and 9 is substantially greater than the spacing of exterior side surfaces 33 and 34 of housing 12.

Each of exterior surfaces 33 and 34 of housing 12 thereby serves as a lateral guidance surface for first arm segment 15 of its corresponding arm. However, the spacing between first arm segments 15 of arms 8 and 9 is such that these arms do not extend laterally beyond the exterior contour of the sole of the boot, nor of the upper surface of the ski.

Figure 6:
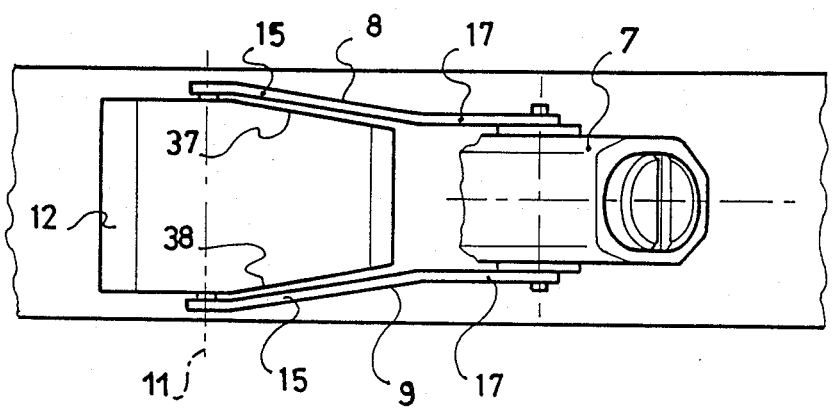
Figure 7:
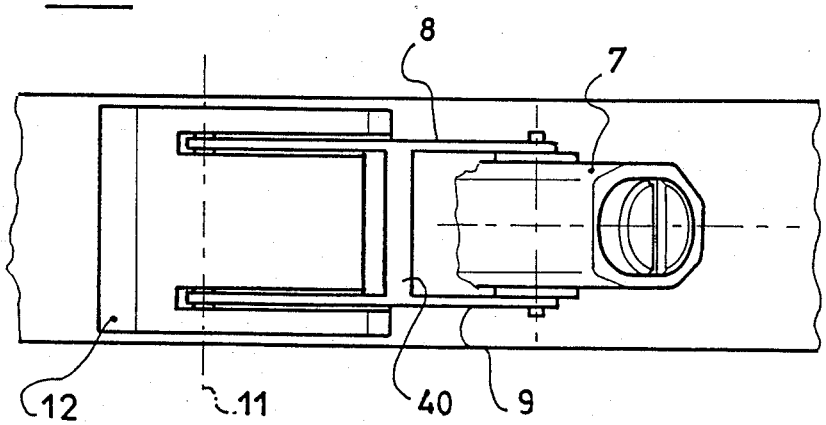

FIGS. 5-7 show specific alternative embodiments of the binding shown in FIG. 1.

FIG. 5 shows second arm segments 17 which are parallel, like first arm segments 15, but spaced closer together. Arms 8 and 9 are further provided with angled intermediate segments 35 linking respective first segments 15 and second segments 17.

In the embodiment of FIG. 6, first arm segments 15 are not parallel to one another, but, rather, are oppositely angled over at least a portion of their length, from axis 11 toward second arm segments 17. In this embodiment, housing 12, itself conforming in shape to arms 8 and 9, is provided with exterior side surfaces 37 and 38, each adjacent to first arm segment 15 of its respective arm 8 and 9. These two surfaces are angled in the same fashion as first arm segments 15, such that exterior surfaces 37 and 38 of housing 12 constitute lateral guidance surfaces for first arm segments 15.

FIG. 7 shows yet another embodiment of the binding of the invention, provided with arms 8 and 9 transversely connected by cross-member 40. Cross member 40 extends substantially horizontally, and connects the two arms 8 and 9 preferably at their respective angles 18.

Figure 8:
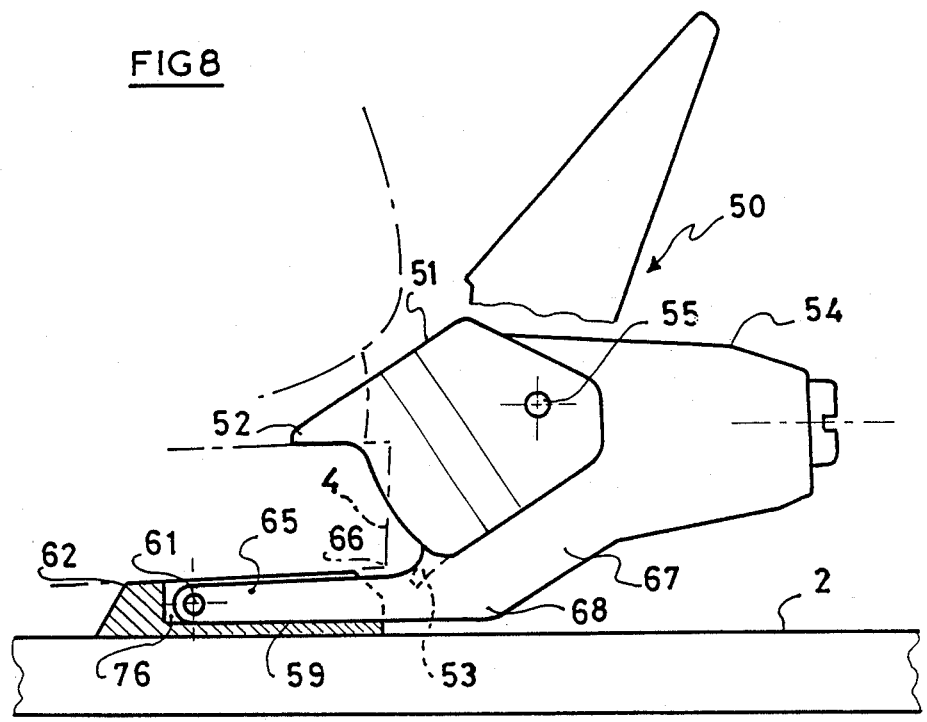
FIG. 8 is a side view of another general embodiment of the binding according to the invention, mounted on a ski.

FIGS. 8-12 show yet another general embodiment of the binding of the invention. Particularly, FIG. 8 shows binding 50, comprising jaw 51 provided with sole grip 52 and boot tongue 53. Jaw 51 is journalled on tranverse axis 55, mounted on body 54.

Binding 50 further comprises elastic energization means, of a type known in the art. These elastic energization means bias jaw 51 down toward the ski; when sole 4 exerts sufficient pressure on jaw 51, these means allow the jaw to pivot upward away from the ski.

One example of such elastic energization means comprises a compression spring situated to push the pressure nose of a piston or a rocker toward a ramp of the jaw. As indicated, such means are known in the art, and therefore are not be described herein in further detail.

Body 54 is connected to the ski by two lateral arms 58 and 59, which are positioned symmetrically along the length of the ski. Both of lateral arms 58 and 59 are affixed to body 54 by their upper ends; the other ends of arms 58 and 59 are journalled at ski 2 around axis of rotation 61.

Like axis of rotation 11 in the general embodiment shown in FIG. 1, axis 61 is preferably mounted on housing 62. Housing 62, in turn, like housing 12 of the previously discussed general embodiment, is mounted on the ski by any suitable means; for example, it may be affixed directly to the ski, or mounted on length adjustment means.

In the binding of the invention, the two arms 58 and 59 which connect body 54 and jaw 51 to the ski are bent; each is provided with a first arm segment 65 which extends, when the binding is disposed in the rest position, rearwardly and substantially horizontally under sole 4 of the boot. Connected to first arm segment 65 is second arm segment 67, which is angled upwardly, toward body 54, to which it is affixed.

As in the general embodiment shown in FIG. 1, angle 68 is situated between first arm segment 65 and second arm segment 67 of each arm, and is adjacent to lower end edge 66 of boot sole 4.

The two lateral arms 58 and 59 are transversely spaced by a distance which is less than the width of the boot sole, measured at its rear end, as well as less than the width of the ski. Accordingly, no part of binding element 50 extends laterally beyond the exterior periphery of the boot, schematically shown by dashed line 70 in FIG. 9, or beyond the upper surface of the ski.

Figure 9:
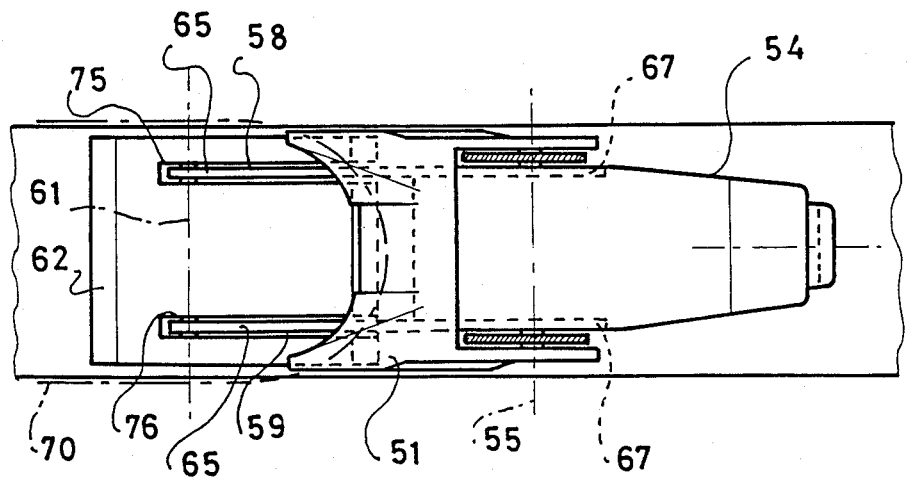
FIG. 9 is a top view of the binding of FIG. 8.

As shown in FIG. 9, housing 62 has, in top view, a substantially rectangular shape, and its width is substantially less than the width of the ski.

Furthermore, housing 62 is provided with recessed areas 75 and 76, situated parallel to one another along length of the ski. These recessed areas extend from adjacent journal axis 61 to the rear end of housing 62, onto which they open. Recessed areas 75 and 76 are separated by a distance corresponding substantially to the spacing between the first segments 65 of arms 58 and 59.

The height of the housing is substantially equivalent to that of a transverse section of a first arm segment 65. Accordingly, in the normal rest position of the binding, as shown in FIG. 8, first segments 65 of the two arms 58 and 59 retract along at least a portion of their length into recessed areas 75 and 76.

Transversely, the width of each recessed area 75 and 76 corresponds substantially to the width of a transverse cross-section of its respective first arm segment; accordingly, the two vertical surfaces which laterally define each groove form transverse guidance surfaces for their respective first arm segments.

During skiing, the pivoting of body 54 around its journal axis 61 causes first segments 65 of arms 58 and 59 to rise partially from their seat in a manner similar to that which has been described with reference to FIG. 3.

Figure 10:
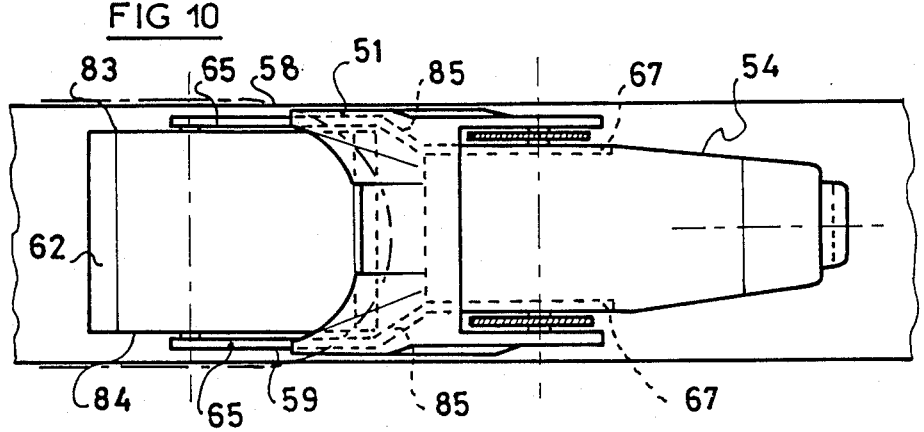
FIG. 10-12 are top views of specific alternative embodiments of the binding of the invention, varying with respect to the relative position of the arms and of the housing.
Figure 11:
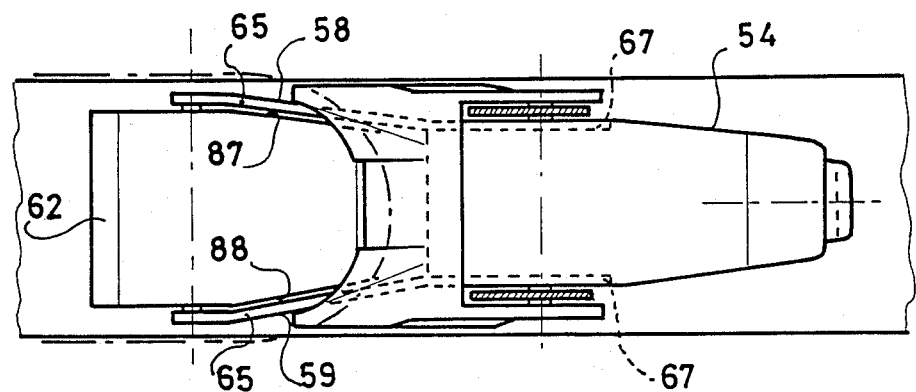
Figure 12:
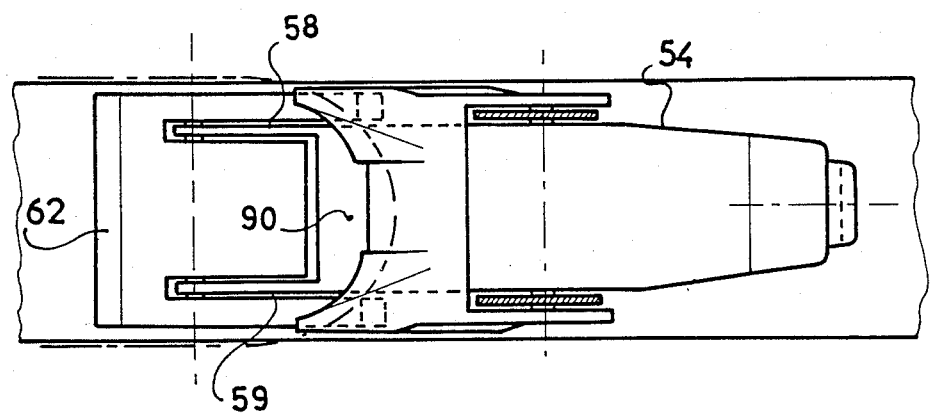

FIGS. 10-12 show specific alternative embodiments of the binding shown in FIG. 8.

The alternative embodiment shown in FIG. 10 is similar to that of FIG. 5, according to which first arm segments 65 of arms 58 and 59 are situated at each side of housing 62, along the length of lateral surfaces 83 and 84. The spacing between the two lateral surfaces 83 and 84 corresponds substantially to the interior spacing between first segments 65 of the two arms 58 and 59, such that surfaces 83 and 84 constitute transverse guidance surfaces for arms 58 and 59.

The lateral distance between the two second segments 67 of arms 58 and 59 is less than the lateral distance between first segments 65. The two segments of each arm are connected by an intermediate segment 85; intermediate sgegments 85 of the respective arms are angled toward one another.

FIG. 11 shows an alternative embodiment similar to that described with reference to FIG. 6. In this embodiment, first segments 65 of arms 58 and 59 are oppositely angled over at leaast a portion of their length. First arm segments 65 extend along the length of exterior side surfaces 87 and 88 of housing 62.

Exterior side surfaces 87 and 88 are oppositely angled in a corresponding manner. Accordingly, these exterior side surfaces 87 and 88 constitute the lateral transverse guidance surfaces for their respective arms 58 and 59.

In the embodiment shown in FIG. 12, the space separating lateral arms 58 and 59 is at least partially occupied by transverse member 90, which connects the two arms.

Preferably, transverse member 90 and arms 58 and 59 are connected in the vicinity of angles 68 of the arms.

FIGS. 13–15 show transverse sections of various embodiments of arms 8 and 9, and 58 and 59.

FIG. 13 shows transverse cross-section 91, which has a substantially rectangular shape, and whose length is situated in a vertical plane.

FIG. 14 shows "L" shaped section 92, having vertically situated major arm 93, and horizontally situated minor arm 94. Minor arm 94 can be oriented towards the interior or towards the exterior of the ski.

FIG. 15 shows section 95, having an elongated shape, provided with reinforcement rib 96 in its central zone. As with minor arm 94, this rib can be oriented towards the interior or towards the exterior of the ski.

The above-indicated shapes for the transverse cross-section of the arms are presented only by way of example, and not limitation; any appropriate transverse cross-section may be used. Preferably, the shape is elongated, with its major dimension being situated in a vertical plane.

FIGS. 16–27 present a feature of the binding of the invention situated at the attachment between the bent arms and the ski. More particularly, these FIGS. show the means for elastically biasing the arms towards the ski, when they have pivoted away from the ski around the axis on which they are journalled.

In particular, such biasing means are provided to facilitate the insertion of the boot, after a voluntary or involuntary release. In effect, these means allow the body in the jaw of the binding to be positioned for insertion of the boot, i.e., as shown in FIG. 4 for the binding 1, without requiring manual intervention to position the first segments of the arms against the ski.

To achieve desired biasing of the arms, the invention provides that the lower ends of the arms are affixed to their their journal axis, and further allows for the rotation of the journal axis with respect to the support housing. Furthermore, the central portion of the journal axis, which is in the form of a cylinder of revolution, is provided with means such as a flattened portion of the axis, or an applied cam, which actuates elastic energization means in the course of rotation of the axis. More particularly, such actuating means push the end of a compression spring; when this pressure is ceased, this spring returns the journal axis and the arms into a stable rest equilibrium position, i.e., particularly that shown particularly in FIGS. 1 and 8.

To facilitate the understanding of the description, FIGS. 16–27 show the embodiment of the binding with reference to FIGS. 1 and 2. This illustration is made only by way of example, and not of limitation; this configuration is equally suitable for use with the other embodiments of the binding of the invention, in particular those described in FIGS. 8–12, such adaptation being within the abilities of one having ordinary skill in the art.

FIG. 16 schematically shows the binding of FIG. 1 in top view, at the level of cross-section plane AA.

This FIG. shows journal axis 11, formed by a pivot in the form of a cylinder of revolution which transversely extends through housing 12. Journal axis 11 is affixed to the lower ends of arms 8 and 9, and is pivotally mounted on housing 12.

In the central zone of axis 11, housing 12 is provided with seat 100, which extends longitudinally from axis 11 toward the rear of the housing. The means for actuating the elastic energization means is shown in the form of flattened portion 101 oriented toward the rear of the housing.

Piston 102 is slidably guided in seat 100, along the length of the ski. Piston 102 is urged towards the front of the ski by spring 103, so as to rest against flattened portion 101 of axis 11.

FIG. 18 shows the functioning of the binding when arms 8 and 9 are partially pivoted around journal axis 11. This pivoting causes both axis 11 and its flattened portion 101 to rotate. The rotation of the flattened portion pushes rear piston 102 toward the rear of the housing, thereby compressing spring 103. When the force which upwardly pivots arms 8 and 9 ceases, spring 103 relaxes, and returns piston 102 towards the front of the housing, thereby also returning journal axis 11 into the initial position shown at FIG. 17.

The intensity of the force exerted by the biasing means is governed by the dimensions of the flattened portion of the axis, and further by the rigidity of the spring.

Actuating means other than flattened portion 101 may be employed; for example, means such as applied cam 105, shown in FIG. 19, are suitable.

FIGS. 20–27 show another general embodiment of binding 1 provided with alternative biasing means.

Figure 20:
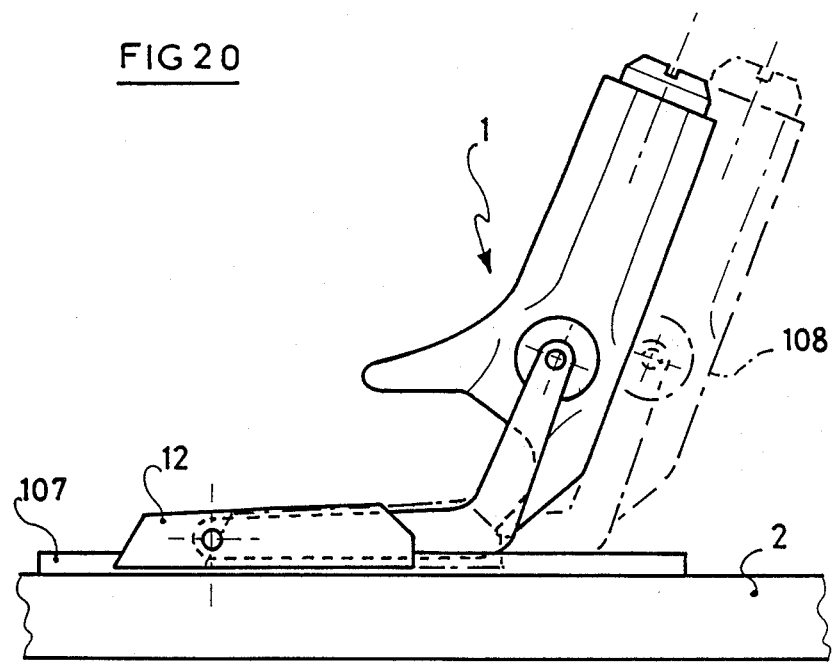
FIG. 20 shows an alternative embodiment of the binding of FIG. 1, wherein the housing is slidably mounted on the ski.

More specifically, FIGS. 20–23 show binding 1 and its housing 12 slidably mounted along slides 107, and provided with elastic energization means forwardly biasing these elements. In FIG. 20, dashed lines 108 show the position of binding 1 and of its housing 12, under the effect of a biasing force.

Figure 21:
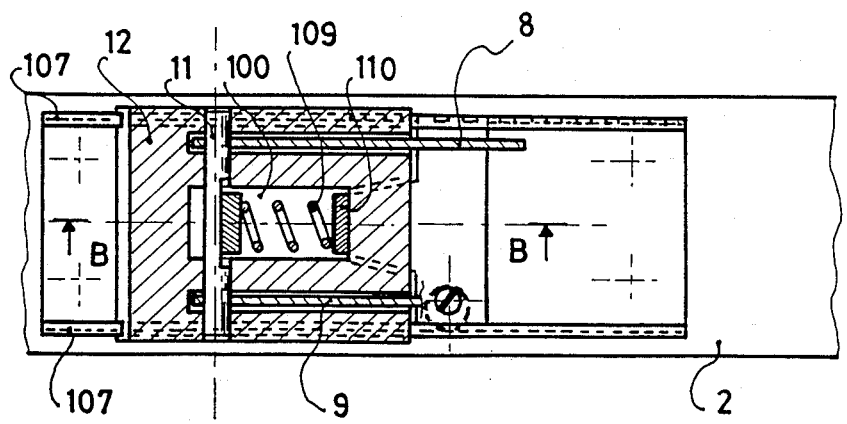
FIG. 21 is a top view in of the housing of the binding of FIG. 20, exposing the means for biasing the arms toward the ski.
Figure 22:
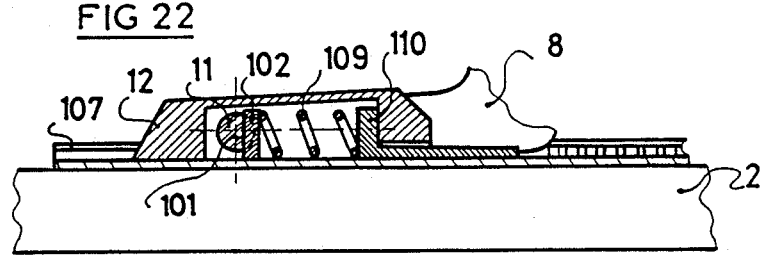
FIG. 22 is a side cutaway view taken along line BB of the binding of FIG. 21.
Figure 23:
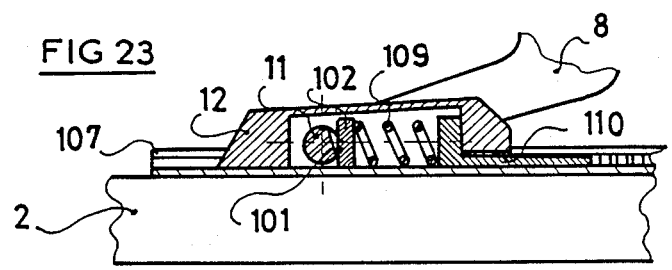
FIG. 23 is another side cutaway view as in FIG. 22 showing the arm in a lifted position.

As in the precedingly described embodiment, the central portion of housing 12 is provided with seat 100, extending rearwardly from axis 11. The elastic energization means, which provide the biasing force, are situated within seat 100. In FIGS. 21–23, these elastic energization means are shown in the form of compression spring 109, oriented along the legnth of the ski. Compression spring 109 is supported at its front end on piston 102, and at its rear end against abutment 110. Abutment 110 is mounted on the ski by any suitable means. For example, it may be affixed directly to the ski, or mounted thereon by length adjustment means.

In a known fashion, under the effect of a presure which causes housing 12 to slide rearwardly, spring 109 compresses. Upon the sensation of this force, spring 109 frontwardly returns to housing 12 and binding 1.

Preferably, the means by which spring 109 and axis 11 are associated is similar to that which has been described with respect to FIGS. 16–18; the linkage preferably comprises flattened portion 101 of axis 11; and longitudinally slidable piston 102 within seat 100.

Thus, spring 109 provides elastic means for returning the binding and its housing to their original position after being subjected to a rearward force, and further provides elastic means for returning arms 8 and 9 to their original position after partial pivoting around axis 11.

FIG. 23 shows arms 8 and 9 pivoted around axis 11; here, also, flattened portion 101 pushes against rear piston 102, which, accordingly, compress spring 109; when this pressure on the spring ceases, it returns the assembly to the position shown in FIG. 22.

Figure 24:
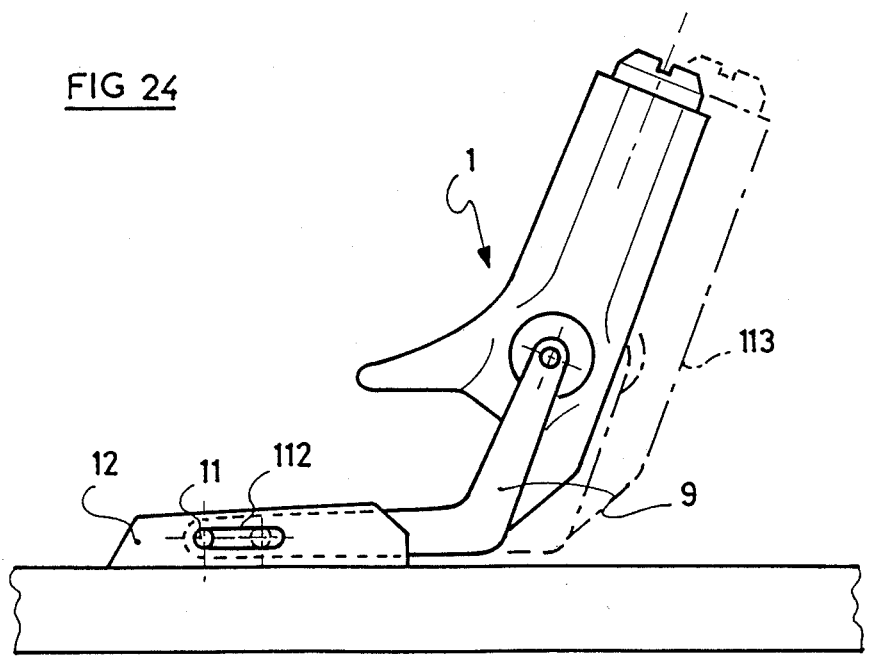
FIG. 24 shows an alternative embodiment of the binding of FIG. 1, wherein the arms are slidably mounted on the housing.
Figure 27:
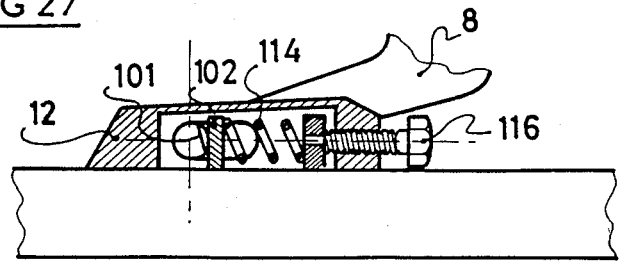
FIG. 27 is another side cutaway view as in FIG. 26, showing the arm in the lifted positon.

FIGS. 24 and 27 show a specific embodiment incorporating elastic energization means, wherein binding 1 and housing 12 are movable longitudinally with respect to one another, and more exactly, where the housing 12 is mounted on the ski, and the body (binding 1) is movable longitudinally with respect to the housing. To this end, housing 12, as employed in this embodiment, is provided not with an orifice for the passage for axis 11, but, rather, with longitudinally extending transverse slot 112, within which axis 11 is adapted to slide.

FIG. 24 schematically illustrates, by means of dashed lines 113, binding 1 disposed in its rearward position, from which elastic energization means elastically return it frontwardly.

Figure 25:
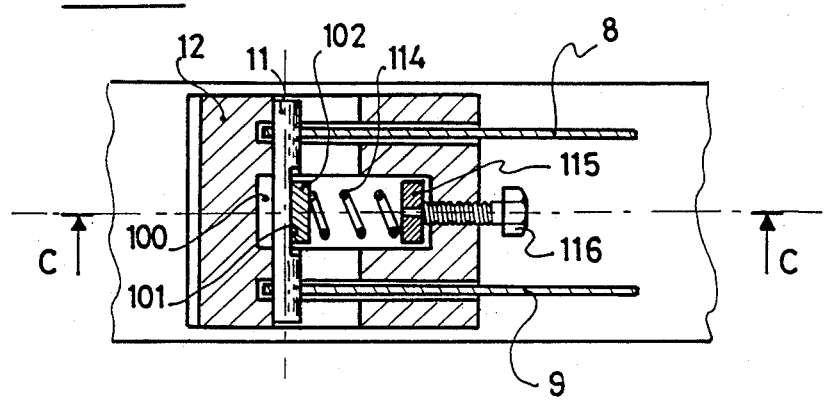
FIG. 25 is a top cutaway view of the housing of the binding of FIG. 24.
Figure 26:
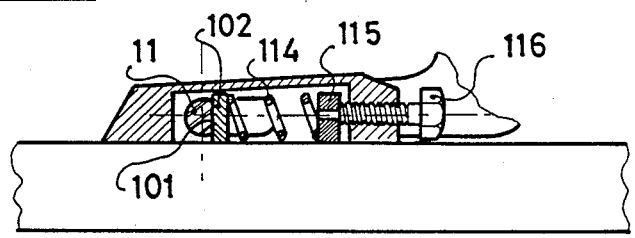
FIG. 26 is a side cutaway view taken along lines CC of the binding of FIG. 25.

These elastic energization means are shown in FIGS. 25-27, in the form of compression spring 114, longitudinally situated in seat 100 of housing 4. Compresson spring 114 is supported at its front end against axis 11, and at its rear end against abutment 15, which is mounted on housing 12.

Abutment 115 may be configured so that its position is longitudinally adjustable by means of screw 116. Alternatively, the portion of the rear exterior surface of housing 12, situated in alignment with seat 100, may be employed in place of abutment 115.

The means by which the front end of spring 114 and journal axis 11 are associated is similar to that described previously with respect to FIGS. 16-19; preferably, these means are a linkage comprising flattened portoin 101 of axis 11, and piston 102 urged frontwardly by spring 114.

FIG. 27 shows arms 8 and 9 in a slightly pivoted position; in this position, flattened portion 101 of axis 11 urges rear piston 102 back against spring 114; as a result, spring 114 will return arms 8 and 9 back to the position shown in FIG. 26 when this pressure against the spring ceases.

For the embodiments of the binding of the invention shown in FIGS. 16-27, the construction of housing 12 itself, which provides for the mounting of arms 8 and 9 and, axis 11, piston 102 and spring 103, 109, or 114, is within the abilities of one having ordinary skill in the art.

Figure 28:
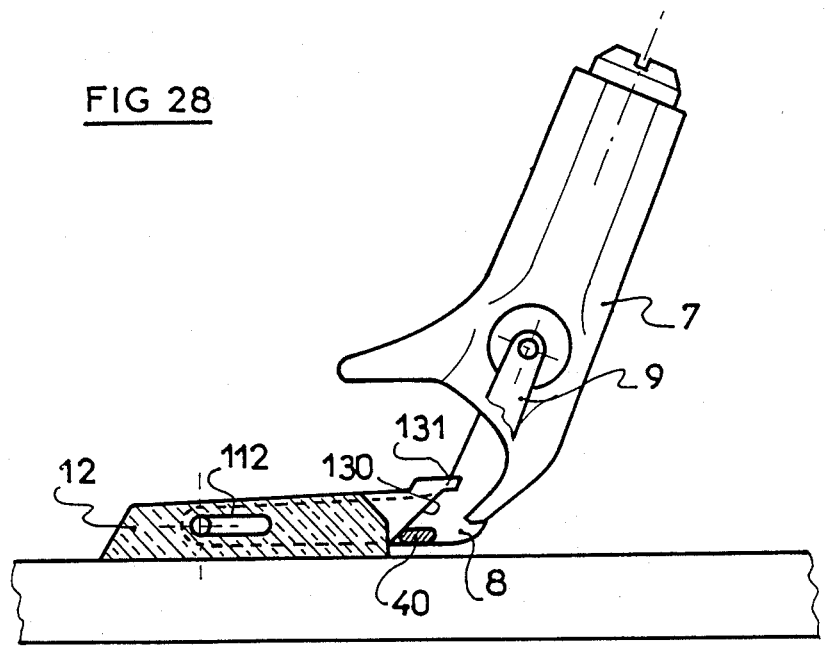
FIG. 28 shows an embodiment of the binding employing alternative means for elastically biasing the arms toward the ski.

FIG. 28 illustrates an embodiment of the binding provided with alternative means for elastically biasing the arms toward the ski.

In this embodiment, body 7, and arms 8 and 9, are adapted to slide towards the rear of housing 12, against the action of a return spring, in a manner similar to that which has been described with reference to FIG. 24. Thus, journal axis 11 of arms 8 and 9 is movable within slot 112 of the body.

Furthermore, as in the embodiment shown in FIG. 7, arms 8 and 9 are connected by a transverse member 40.

Housing 12 furthermore is provided in its rear portion with ramp 130. Transverse member 40 presses against ramp 130 when the boot is not present, thereby causing the spring to press body 7, arms 8 and 9, and transverse member 40 back toward the front of the ski. Ramp 130 acts in concert with the elastic energization means in providing for the upward pivoting of arms 8 and 9; in other words, the rising of transverse member 40 on ramp 130 causes axis 11 to move rearwardly in slot 112; this movement, in turn, compresses the spring.

Figure 29:
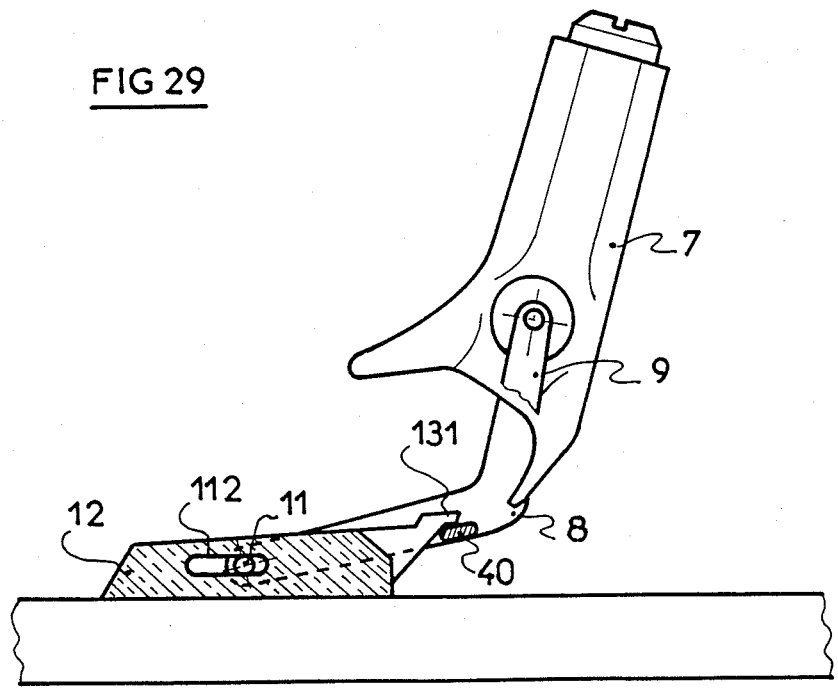
FIGS. 29 and 30 show two operational aspects of the binding of FIG. 29.

FIG. 29 shows body 7 and arms 8 and 9 pivoted upwardly, with axis 11 having moved rearwardly in slot 112. Upon cessation of the pressure compressing the spring, the spring will return arms 8 and 9 toward the ski, and will further move axis 11 forward in the slot.

Preferably, ramp 130 is provided in its upper portion with lip, or flange 131. Lip 131 serves to limit the upward pivoting movement of transverse member 40.

Figure 30:
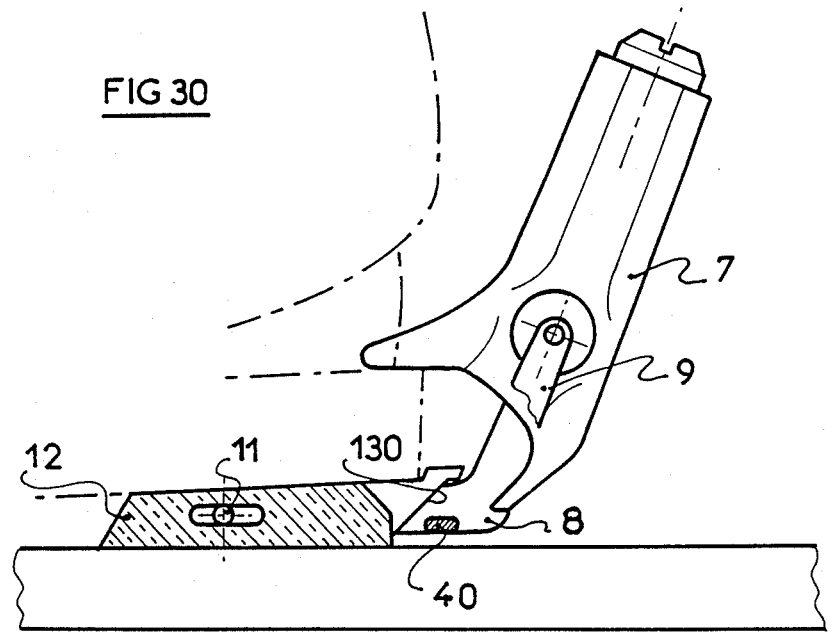

Furthermore, as show in FIG. 30, positioning of a boot in the binding biases the rear binding for retreat, thereby causing a separation of transverse member 40 from ramp 130.

In this manner, the arms are elastically biased towards the ski when the boot is present in the binding.

Figure 31:
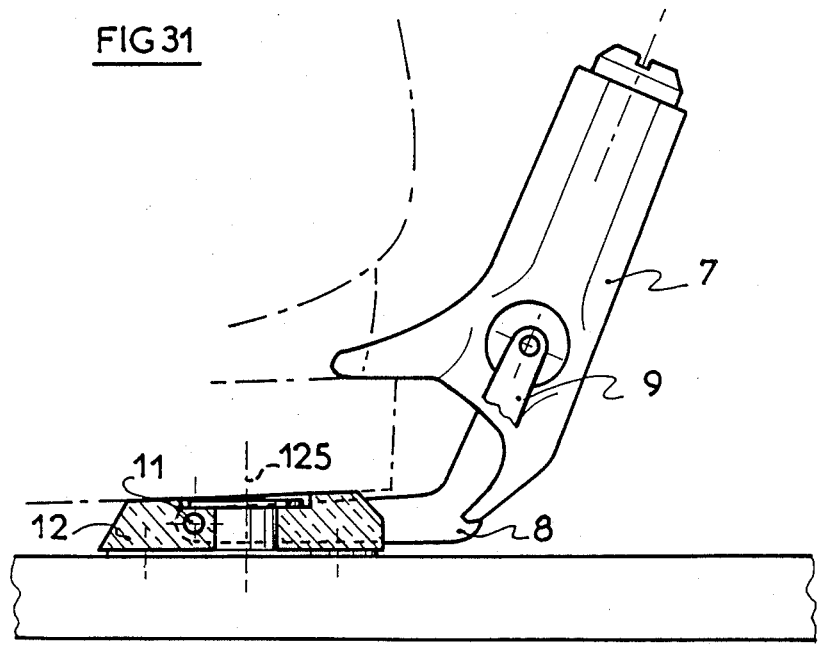
FIG. 31 shows an alternative embodiment of the binding of FIG. 1, at the level of the housing.

FIG. 31 illustrates another embodiment of the binding of the invention shown in FIG. 1. According to this embodiment, housing 12 is pivotably mounted around substantially vertical axis 125 situated in a vertical plane defined by the length of the ski.

Figure 32:
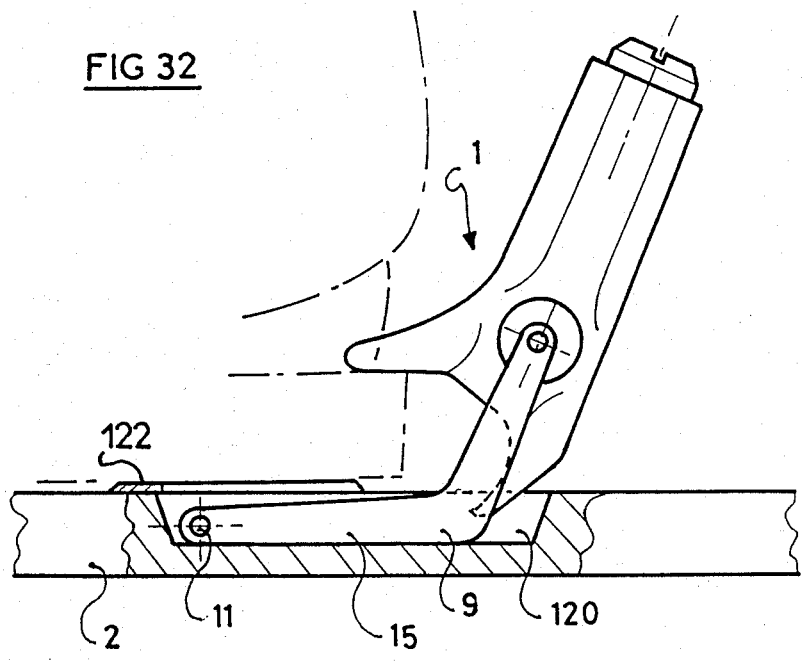
FIGS. 32 and 33 are alternative embodiments of the bindings of FIGS. 1 and 8, respectively, at the level of the attachment between the ski and the arms.

The embodiment of the invention shown in FIG. 32 is not provided with a housing for the axis on which arms 8 and 9 are journalled; rather, arms 8 and 9 are mounted at their lower ends directly on ski 2; axis 11 is also mounted directly on the ski. The upper surface of the ski is provided with two grooves 120, in which first segments of arms 8 and 9 retract. The lateral surfaces defining groove 120 constitute transverse guidance surfaces for first segments 15 of arms 8 and 9.

Figure 33:
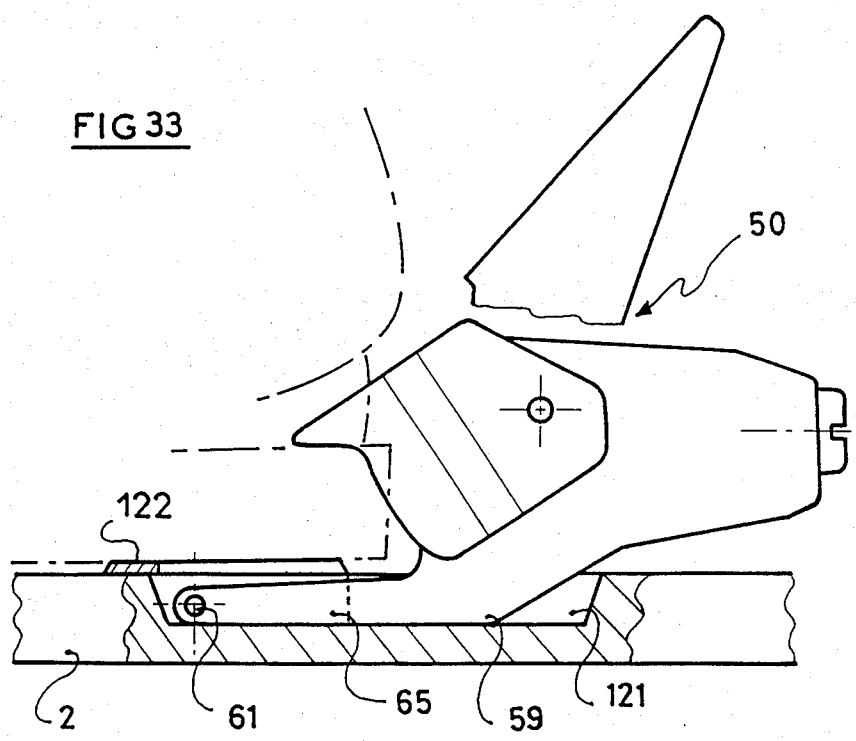

In a similar manner, FIG. 33 shows binding 50 provided with first segments 65 of arms 58 and 59, retracted within grooves 121 of ski 2. Journal axis 61 of arms 58 and 59 is mounted directly on the ski itself.

In these latter two described embodiments, plate 122, extending along the upper surface of the ski, may be provided for the heel of the boot to rest on.

It is again emphasized, as previously pointed out, that the binding of the invention is suitable not only for rear binding, but also for front binding of a boot against a ski.

It is further understood that although the invention has been specifically described with reference to particular means and embodiments, the foregoing description is that of preferred embodiments of the invention. The invention is not limited to the particulars disclosed, but extends to all equivalents, and various changes and modifications may be made in the invention without departing from the spirit and scope thereof.

What is claimed is:

1. A binding for retaining a boot on a ski comprising:
   (a) means for pressing one end of said boot against said ski;
   (b) means for supporting said pressing means;
   (c) at least two connecting members comprising means for connecting said supporting means to said ski, said at least two connecting members being spaced apart by a distance less than the width of a sole of said boot end which is adapted to be retained by said binding, wherein said at least two connecting members are separated by a distance less than the width of the ski, wherein said at least two connecting members comprise two arms mounted on said ski to pivot into and out of a retracted position and wherein, in said retracted position, at least a portion of each arm is positioned under a surface for supporting said boot end, and wherein said two arms are journalled about an axis substantially perpendicular to the length of said ski, each of said arms comprising a first arm segment mounted on an axle for pivotal movement about said axis, said axle being located beneath a surface for supporting said boot end and a second arm segment connected to said supporting means, wherein, in said retracted position, at least a portion of each of said first arm segments is positioned under said surface for supporting said boot end, and said second arm segments are angled upwardly towards said supporting means.

2. The binding defined by claim 1 wherein said two arms are mounted to pivot about an axis located beneath an area of said surface on which said boot end is supported.

3. The binding defined by claim 1 wherein said two arms are mounted against movement relative to said ski about a substantially vertical axis.

4. A binding for retaining a boot on a ski comprising:
  (a) means for pressing one end of said boot against said ski;
  (b) means for supporting said pressing means;
  (c) at least two connecting members comprising means for connecting said supporting means to said ski, said at least two connecting members being spaced apart by a distance less than the width of a sole of said boot end which is adapted to be retained by said binding, wherein said at least two connecting members are separated by a distance less than the width of the ski, wherein said at least two connecting members comprise two arms mounted on said ski to pivot into and out of a retracted position and wherein, in said retracted position, at least a portion of each arm is positioned under a surface for supporting said boot end, wherein said two arms are journalled about an axis substantially perpendicular to the length of said ski, each of said arms comprising a first arm segment mounted to an axle for pivotal movement about said axis, and a second arm segment connected to said supporting means, wherein, in said retracted position, at least a portion of each of said first arm segments is positioned under said surface for supporting said boot end, and said second arm segments are angled upwardly towards said supporting means.

5. The binding as defined by claim 4 wherein said pressing means and said supporting means are stationarily mounted with respect to one another, and said supporting means and said second arm segments are pivotably mounted with respect to one another.

6. The binding as defined by claim 5 wherein said axis extends through said ski, and said ski comprises recessed areas extending along at least a portion of the length of the ski, at least a portion of said first arm segments, along their respective lengths, being positioned in said recessed areas when said arms are positioned in said retracted position.

7. The binding as defined by claim 5 wherein said axis extends through a housing which is adapted to be mounted on said ski, said housing comprising at least one surface to which each of said first arm segments is attached, wherein said surface for supporting said boot end includes the upper surface of said housing.

8. The binding as defined by claim 7 wherein said housing is attached to the upper surface of a ski.

9. The binding as defined by claim 7 wherein said housing comprises recessed areas, wherein at least a portion of said first arm segments, along their respective lengths, are positioned in said recessed areas when said arms are positioned in said retracted position.

10. The binding as defined by claim 9 wherein said recessed areas are spaced inwardly from opposite exterior sides of said housing.

11. The binding as defined by claim 9 wherein:
  (a) the first segment of each arm is connected to its second segment; and
  (b) said two arms are connected by a cross-member affixed to each of said arms at an intermediate point of connection between said first and second arm segments.

12. The binding as defined by claim 7 wherein said at least one surface, to which each of said first arm segments is attached, comprises two exterior sides of said housing.

13. The binding as defined by claim 12 wherein said first arm segments are parallel to one another and said second arms segments are parallel to one another, said first arm segments being spaced apart by a distance greater than the distance spacing said second arm segments apart, said first and second arm segments being connected by angled intermediate arm segments.

14. The binding as defined by claim 12 wherein said two exterior sides of said housing are oppositely angled, and wherein at least a portion of said first arm segments are oppositely angled.

15. The binding as defined by claim 4 wherein said supporting means and said second arm segments are stationarily mounted with respect to one another, and said pressing means and said supporting means are pivotably mounted with respect to one another.

16. The binding as defined by claim 13 wherein said axis extends through said ski, and said ski comprises recessed areas, wherein at least a portion of said first arm segments, along their respective lengths, are positioned within said recessed areas when said arms are positioned on said retracted position.

17. The binding as defined by claim 15 wherein said axis extends through a housing which is adapted to be mounted on said ski, said housing comprising at least one surface to which each of said first segments is attached, wherein said surface for supporting said boot end includes the upper surface of said housing.

18. The binding as defined by claim 17 wherein said housing is attached to the upper surface of the ski.

19. The binding as defined by claim 17 wherein said housing comprises recessed areas, wherein at least a portion of said first arm segments, along their respective lengths, are positioned in said recessed areas when said arms are positioned in said retracted position.

20. The binding as defined by claim 19 wherein said recessed areas are spaced inwardly from opposite exterior sides of said housing.

21. The binding as defined by claim 19 wherein:
  (a) the first segment of each arm is affixed to its second segment; and
  (b) said two arms are connected by a cross-member affixed to each of said arms at an intermediate point of connection between said first and second segments.

22. The binding as defined by claims 17, wherein said at least one surface to which each of said first arm segments is attached comprises two exterior sides of said housing.

23. The binding as defined by claim 22 wherein said first arm segments are parallel to one another and said second arm segments are parallel to one another, said first arm segments being spaced apart by a distance greater than the distance spacing said second arm segments apart, said first and second arm segments being connected by angled intermediate segments.

24. The binding as defined by claim 22 wherein said two exterior sides of said housing comprise respective portions which converge along the length of the ski, and wherein at least a portion of each of said first arm segments converge along the length of the ski.

25. The binding as defined by claim 4 wherein said binding further comprises means for biasing said arms towards said ski.

26. The binding as defined by claim 4 wherein said axle is mounted on a housing mounted to pivot on said ski, said housing comprising at least one surface to which each of said first arm segments is attached, wherein said surface for supporting said boot end includes the upper surface of said housing.

27. The binding as defined by claim 4 wherein said supporting means and said second arm segments are stationarily mounted with respect to one another, and said pressing means and said supporting means are pivotably mounted for movement in a substantially vertical plane with respect to one another.

28. The binding defined by claim 17 wherein said housing is adapted to be fixed against relative movement with respect to said ski.

29. A binding for retaining a ski boot on a ski, comprising:
(a) a jaw for retaining one end of said boot, said jaw being adapted to move in at least one direction along a substantially vertical plane;
(b) elastic energization means for biasing said jaw towards the ski;
(c) means for supporting said jaw, and at least two arms aligned along the length of the ski and spaced apart by a distance less than the width of the sole of said one boot end, said at least two arms connecting said supporting means to said ski and being journalled about an axis substantially perpendicular to the length of said ski in order to pivot into and out of a retracted position, each arm comprising, when in said retracted position, a first arm segment positioned under a surface for supporting said boot end, and aligned substantially parallel to the legnth of said ski, and a second arm segment angled upwardly towards said supporting means.

30. The binding as defined by claim 29 wherein said jaw is affixed to said supporting means, and said supporting means is journalled on said arms.

31. The binding as defined by claim 29 wherein said jaw is journalled on said supporting means, and said supporting means is affixed to said arms.

32. The binding as defined by claim 29 wherein said axis extends through a housing mounted on said ski, said housing comprising at least one surface to which each of said first arm segments is attached, wherein said surface for supporting said boot end includes the upper surface of said housing.

33. The binding as defined by claim 32 wherein said housing comprises two recessed areas extending along at least a portion of the length of said housing, wherein at least a portion of each of said first arm segments, when in its retracted position, is positioned in one of said recessed areas.

34. The binding as defined by claim 32 wherein said arms are vertically pivotable.

35. The binding as defined by claim 32 wherein said first arm segments are substantially parallel to one another and said second arm segments are substantially parallel to one another, said first arm segments being spaced apart by a distance greater than the distance spacing said second arm segments apart, said first and second arm segments being connected by angled intermediate arm segments.

36. The binding as defined by claim 32 wherein said housing includes two exterior side surfaces having respective portions which converge along the lenth of the ski, and wherein at least a portion of said first arm segments converge along the length of the ski.

37. The binding as defined by claim 32 wherein said arms are connected by a cross-member.

38. The binding as defined by claim 32 further comprising an axle extending along said axis attached to free ends of said first arm segments and pivotably mounted on said housing, wherein said elastic energizing means comprise means for biasing said axle.

39. The binding as defined by claim 38 wherein said axle comprises a substantially cylindrical member having a planar surface between two ends of said axle, said elastic energizing means comprising a compression spring which abuts said planar surface.

40. The binding as defined by claim 38 wherein said axle comprises an eccentric member which abuts a compression spring.

41. The binding as defined by claim 38 wherein said elastic energizing means comprises means for biasing said binding towards said boot end adapted to be retained by said binding.

42. The binding as defined by claim 32 further comprising an axle extending along said axis for journalling said at least two arms about said axis, wherein:
(a) said housing includes an inclined ramp, said axle being slidably mounted in a slot in said housing, said slot extending in a direction substantially parallel to the length of the ski;
(b) said biasing means further comprises means for biasing said housing along the length of the ski towards said support surface; and
(c) said two arms being connected by a cross-member which is adapted to slidably abut said ramp, wherein said cross-member abuts said ramp when no boot is positioned on said surface, said cross-member comprising means for compressing said elastic energization means when said cross-member rises up said ramp.

43. The binding as defined by claim 42 wherein said inclined ramp and said housing comprise a single member.

44. The binding as defined by claim 42 wherein said inclined ramp and said housing comprise two members attached to each other.

45. The binding as defined by claim 32 wherein said housing is vertically mounted to pivot on an axis perpendicular to the length of said ski.

46. The binding as defined by claim 29 wherein said axis extends through said ski, and said ski comprises recessed areas extending along at least a portion of the length of said ski, said first arm segments being positioned in said recessed areas when in said retracted position.

47. The binding defined by claim 29 wherein said axis is located beneath an area of said surface on which said boot end is supported.

48. The binding defined by claim 29 wherein said two arms are mounted against movement relative to said ski about a substantially vertical axis.

49. A binding for retaining a boot on a ski comprising:
(a) means for pressing one end of said boot against said ski;
(b) means for supporting said pressing means;
(c) at least two arms for connecting said supporting means to said ski, said at least two arms being spaced apart by a distance less than the width of a sole of said boot end which is adapted to be retained by said binding, wherein said at least two arms are separated by a distance less than the width of the ski, wherein said at least two arms are mounted on said ski to pivot into and out of a retracted position, wherein, in said retracted position, at least a portion of each arm is positioned under a surface for supporting said boot end, wherein said at least two arms are journalled about an axis substantially perpendicular to the length of said ski, each of said arms comprising a first arm segment mounted on an axle for pivotal movement with said axle about said axis, and a second arm segment connected to said supporting means, wherein, in said retracted position, at least a portion of each of said first arm segments is positioned under said surface for supporting said boot end, and said second arm segments are angled upwardly towards said supporting means; and
(d) means for biasing said arms towrads said ski comprising elastic energization means engaged with said axle.

50. The binding as defined by claim 49 wherein said elastic energization means comprises a compression spring aligned substantially perpendicularly to said axis, said compression spring comprising means for biasing said axle and adapted to being compressed by the pivoting of said axle.

51. The binding as defined by claim 50 wherein said axle comprises a substantially cylindrical member having a planar surface between two ends of said axle, and wherein said compression spring abuts said planar surface.

52. The binding as defined by claim 50 wherein said axle comprises an eccentric member which abuts said compression spring.

53. The binding as defined by claim 50 wherein said axle is mounted on a housing which is adapted to be mounted on said ski.

54. The binding as defined by claim 53 wherein:
(a) said housing is slidably mounted along at least a portion of the length length of said ski;
(b) said compression spring comprises means for biasing said housing along the length of the ski in one direction towards said boot end when said boot is positioned on an upper ski surface; and
(c) said axle comprises means for compressing said spring against abutment means mounted on said ski.

55. The binding as defined by claim 54 wherein said abutment means is mounted in a stationary position on said ski.

56. The binding as defined by claim 54 wherein said abutment means is mounted on means for adjusting the position of said abutment means along the longitudinal extent of the ski.

57. The binding as defined by claim 53 wherein said axle is mounted for sliding movement in a slot in said housing, said slot extending in a direction substantially parallel to the length of said ski, said compression spring comprising means for biasing said axle along the length of said ski towards said boot end, said axle comprising means for compressing said spring against abutment means for compressing said spring against abutment means mounted on said housing.

58. The binding as defined by claim 57 wherein said housing is mounted in a stationary position with respect to said ski.

59. The binding as defined by claim 57 wherein said abutment means is mounted in a stationary position with respect to said housing.

60. The binding as defined by claim 57 wherein said abutment means is mounted on means for adjusting the position of said abutment means in said housing.

61. The binding as defined by claim 60 wherein said position-adjusting means comprises a screw mounted in said housing.

62. The binding as defined by claim 57 wherein said abutment means comprises an interior surface of said housing.

63. The binding as defined by claim 57 wherein said housing includes an inclined arm, and said two arms are connected by a cross-member which is adapted to slidably abut said ramp when said compression spring is not compressed, such that pivoting said arms raises said cross-member along said ramp and retaining a boot end on said ski spaces said cross-member from said ramp.

64. The binding as defined balong said ramp and retaining a boot end on said ski spaces said cross-member from said ramp.

* * * * *

UNITED STATES PATENT AND TRADEMARK OFFICE
CERTIFICATE OF CORRECTION

PATENT NO. : 4,863,186

DATED : September 5, 1989

INVENTOR(S) : Pierre RULLIER et al.

It is certified that error appears in the above-identified patent and that said Letters Patent is hereby corrected as shown below:

At column 5, line 41, change "legth" to ---length---.
At column 12, line 63, delete ";" after "11".
At column 13, line 24, change "Compresson" to ---Compression---.
At column 13, line 36, change "portoin" to ---portion---.
At column 14, line 12, change "show" to ---shown---.
At column 19, line 30 (claim 49, line 27), change "towrads" to ---towards---.
At column 20, line 41 (claim 63, line 2), change "arm" to ---ramp--- before "and".
At column 20, lines 47, 48 and 49 (claim 64, lines 1, 2 and 3), change "balong said ramp and retaining a boot end on said ski spaces said cross-member from said ramp" to ---by claim 63 wherein said ramp is provided with a lip to limit the rise of said cross-member during the pivoting of said arms---.

Signed and Sealed this

Twelfth Day of May, 1992

Attest:

DOUGLAS B. COMER

Attesting Officer

Acting Commissioner of Patents and Trademarks